United States Patent [19]

Gaudette et al.

[11] 4,338,460

[45] Jul. 6, 1982

[54] PROCESS FOR PREPARING CHELATING AGENTS

[75] Inventors: Roger R. Gaudette, Hudson, N.H.; John L. Ohlson, Bedford; Patricia M. Scanlon, Arlington, both of Mass.

[73] Assignee: W. R. Grace & Co., New York, N.Y.

[21] Appl. No.: 179,805

[22] Filed: Aug. 20, 1980

Related U.S. Application Data

[60] Continuation-in-part of Ser. No. 924,019, Jul. 12, 1978, abandoned, which is a continuation of Ser. No. 766,285, Feb. 7, 1977, abandoned, which is a division of Ser. No. 630,792, Nov. 11, 1975, Pat. No. 4,069,249.

[51] Int. Cl.$^3$ .......................................... C07C 101/72
[52] U.S. Cl. .............................. 562/448; 260/501.12; 260/507 R; 544/335
[58] Field of Search .................... 562/448; 260/507 R, 260/501.12

[56] References Cited

U.S. PATENT DOCUMENTS

| Re. 23,904 | 12/1954 | Bersworth | 562/448 |
|---|---|---|---|
| 2,624,757 | 1/1953 | Bersworth | 562/448 |
| 2,717,263 | 9/1955 | McKinney et al. | 562/448 |
| 2,763,680 | 9/1956 | Sailmann | 260/507 |
| 2,967,196 | 1/1961 | Kroll et al. | 568/448 |
| 3,394,174 | 7/1968 | Feigin | 260/509 |
| 3,394,184 | 7/1968 | Bailey . | |
| 3,632,637 | 1/1972 | Martell . | |
| 3,742,002 | 6/1973 | Ohlson et al. . | |
| 3,988,367 | 10/1976 | Gaudette et al. . | |
| 4,069,249 | 1/1978 | Gaudette et al. | 260/501.12 |
| 4,152,345 | 5/1979 | Gaudette et al. | 260/439 R |
| 4,225,502 | 9/1980 | Gaudette et al. | 260/465 E |

OTHER PUBLICATIONS

Jakublee et al., *Amino Acids, Peptides and Proteins*, John Wiley & Sons, pp. 23, 25, (1977).
Greenstein et al., *Chemistry of the Amino Acids*, John Wiley & Sons, p. 478, (1961).
Morrison et al., *Organic Chemistry*, 2nd Edition, Allyn and Bacon, p. 1103, (1966).
Chaberek et al., *Organic Sequestering Agents*, John Wiley & Sons, p. 63, (1959).

*Primary Examiner*—G. T. Breitenstein
*Attorney, Agent, or Firm*—Ronald A. Bleeker; Donald G. Marion

[57] ABSTRACT

A process for preparing in high yield an isolable orthohydroxydiaminodicarboxylic acid which is useful as a metal chelating agent. The process comprises reacting a phenol (or mixture of phenols), a diaminodicarboxylic acid (or acid source), and a formaldehyde source in a medium having an acidic pH.

7 Claims, No Drawings

PROCESS FOR PREPARING CHELATING AGENTS

This application is a continuation-in-part based on United States patent application Ser. No. 924,019 filed on July 12, 1978; now abandoned, which was a continuation of application Ser. No. 766,285 filed Feb. 7, 1977; now abandoned, which was a division of application Ser. No. 630,792 filed Nov. 11, 1975, now U.S. Pat. No. 4,069,249. The desired end products of the process claimed in the present application are the subject of U.S. Pat. No. 4,069,249.

This invention relates to the field of metal chelating agents and, more particularly, to a process for obtaining in high, soluble yield an ortho-hydroxydiaminodicarboxylic acid which is useful as a strong metal chelating agent. Metal chelating agents are well known to be useful for supplying trace elements to growing plants, for inclusion in metal plating baths, for removing "rust" stains from various types of surfaces, and for removing impurities from water. The present invention is directed to a process for efficiently obtaining a particular class of chelating agents in unexpectedly high yield by conducting the reaction at an acidic pH and by employing particular diamino acids.

More particularly, this invention is directed to a process for preparing in high isolable yield a compound having the general formula

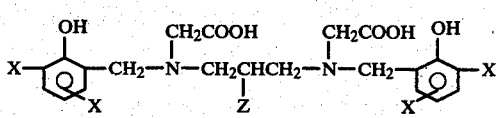

wherein Z is H or OH and each X is a member selected from a group consisting of hydrogen; an alkyl group having 1-4 carbon atoms; —COOH; and —SO$_3$M, wherein M is an alkali metal ion, ½ an alkaline earth metal ion; or an ammonium ion having the formula

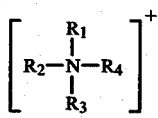

in which each of R$_1$, R$_2$, R$_3$, and R$_4$ is hydrogen, an alkyl group having 1-4 carbon atoms, or a hydroxyalkyl group. The process comprises reacting in an acidic pH medium:

(a) a phenol or mixture of phenols having the formula

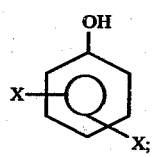

(b) a dimino acid having the formula

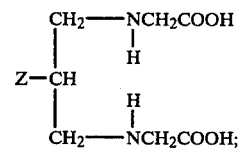

a diamino acid source having the formula

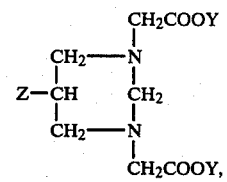

wherein Y is an alkali metal ion, ½ of an alkaline earth metal ion or an ammonium ion having the formula

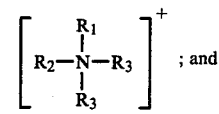

(c) a formaldehyde source selected from the group consisting of an aqueous formaldehyde solution, trioxane, and paraformaldehyde in a inert solvent.

In order to produce an end product of this type utilizing ortho-substitution, it has generally been considered necessary to react (1) a para-substituted phenol (or mixtures of phenols), a diamino acid (or acid source), and a formaldehyde source under alkaline conditions, as in U.S. Pat. No. 2,967,196, particularly as described in Column 2, lines 24-58; (2) a diaminoacid (or diamine precursor) with an ortho-hydroxybenzyl halide, as in U.S. Pat. No. Re 23,904, Example V, and U.S. Pat. No. 3,632,637 (see Column 3, lines 3-23); or (3) an ortho-hydroxybenzaldehyde from a diamine followed by reduction and carboxymethylation, as mentioned in U.S. Pat. No. 3,632,637 and described in Example 1 of the present disclosure. It has now been discovered that conducting the reaction of a phenol and formaldehyde with the specific, aforementioned trimethylenebridged diaminoacids at an acidic pH directs ortho-substitution. This direction and other major and unexpected process advantages may be obtained without blocking the para-position or using ortho-hydroxy benzyl halides or aldehydes that unambiguously give ortho products.

U.S. Pat. Nos. 2,717,263; 2,763,680, 3,394,184 and 3,742,002 further show the need of para-blocking and-/or unambiguous ortho-forming reagents with different amino acids. U.S. Pat. Nos. 2,717,263 and 3,394,174 are mentioned to illustrate that when para-blocking is not used in condensing other amino acids with phenol and formaldehyde under alkaline conditions, unknown substitution occurs, as indicated by the structures drawn.

We have found that reacting amino acids with phenol and formaldehyde even under acidic conditions, does not necessarily give good, isoluble yields of the desired, ortho product. Even the ethylene-bridged diamino acid N, N'-ethylenediaminediacitic acid under acidic conditions gave nearly all 4-(o-hydroxybenzyl)-2 piperazone-1-acetic acid,

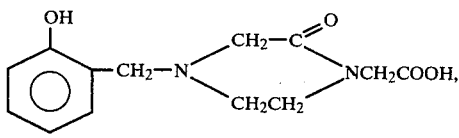

useless as an iron chelating agent (see Example 12).

Unexpectedly, the reaction of phenols with formaldehyde and the trimethylene-bridged diamino acids of the present disclosure in acidic media gives excellent yields of the ortho-substituted products that are strong iron chelating agents.

It has thus been discovered that when the mixture of the above diaminoacids and formaldehyde is maintained at a pH of about 2 to 6, the added phenol unexpectedly undergoes preferential reaction at the ortho ring position rather than at the usually more reactive para ring position. It is common in condensation reactions of this type to block the more reactive para position in order to have the desired substitution at the ortho position. However, in the present process, there is no need to block the para position to promote reaction at the ortho position. This fortuitous and unexpected result with the above particular diaminoacids permits the synthesis of condensation products without useless substitution on the phenol rings. Ortho substitution is necessary for the product to be effective as an iron chelating agent. A pH of less than 2 is operable but is not considered to be practical from a commercial point of view.

A further unexpected advantage of maintaining such an acidic pH is the significantly greater yield of the desired end product which is obtained. We have found that the synthesis and decomposition of the desired end product, as well as other ortho-hydroxybenzylamino acids, occur simultaneously as competing reactions. It has now been found that alkaline pH's classically used promote degradation of ortho-hydroxybenzyl amino acids, and in fact, the end product decomposes if heated in an alkaline medium. On the other hand, reaction in an acidic medium favors formation of the desired end product, and not degradation, and thereby significantly increases the yield obtained.

In addition, the use of an acidic medium also helps to improve the yield of the desired end product by suppressing undesirable side reactions which lead to the formation of unwanted and unreactive by-products. Thus, unless an acidic pH is used, the formaldehyde and particular diaminoacids will react to form a hexahydropyrimidine product which is not reactive with the phenol reactant. The result is an unreactive mixture of the phenol with the reaction product of the formaldehyde and the diaminoacid. It has now been found that formation of this unwanted by-product is suppressed by the use of an acidic pH. See U.S. Pat. No. 3,988,367. This provides yet another process advantage which tends to increase the yield of the desired end product.

The general formula of the desired end product which is the subject of this application, as well as the general formulas of the three reactants which are combined in an acidic medium to give this desired product in high yield, have been previously set forth herein. As will be seen from the following Examples and Procedures, certain preferred embodiments exist within these general formulas. The following Examples were actually run; the Procedures, while not actually run, will illustrate certain embodiments and features of the invention.

As used herein the term "a hydroxyalkyl group having 1-4 carbon atoms" means a group such as (a) $-CH_2OH$ (b) $-CH_2CH_2OH$; (c) $CH_3CHOH$;

(d) $-CH_2CH_2CH_2OH$; (e) $CH_3CHCH_2OH$;

(f) $CH_3CH_2CHOH$; (g) $-CH_2CHOH$; (h) $CH_3COH$;
                                         $CH_3$         $CH_3$ (i) $-CH_2CH_2CH_2CH_2OH$; (j) $CH_3CHCH_2CH_2OH$;

(k) $CH_3CH_2CHCH_2OH$; (l) $CH_3CH_2CH_2CHOH$;

(m) $-CH_2CHCH_2OH$; (n) $CH_3CCH_2OH$; (o) $CH_3CHCHOH$;
     $CH_3$              $CH_3$              $CH_3$ (p) $-CH_2CH_2CHOH$; (q) $CH_3CHCHOH$; (r) $CH_3CH_2CHOH$;
     $CH_3$              $CH_3$             $CH_2$ (s) $CH_3CH_2COH$; and (t) $-CH_2COH$.
     $CH_3$                 $CH_3$ As used herein the term "HBPD" means N,N'-di(o-hydroxybenzyl)-1,3-propanediamine-N,N'diacetic acid.

As used herein the term "HYPDANa₂" means disodium hexahydropyrimidine-1,3-diaceate.

As used herein the term "PDDA" means 1,3-propanediamine-N,N'-diacetic acid.

As used herein the term "PDDA-OH" means 1,3-diamino-2-propanol-N,N'-diacetic acid.

As used herein "HBPDNaFe" or "HBPDFeNa" means the iron (III) chelate of the sodium salt of HBPD.

As used herein "HBPDFe₂H₂" means the iron (II) chelate of the acid form of HBPD.

As used herein "HBPDFeNaH" means the iron (II) chelate of the monosodium salt of HBPD.

As used herein the term "HBPDFeH" means the iron (III) chelate of HBPD.

As used herein the term "HBPD-OL" means N,N'-di(o-hydroxybenxyl)-1,3-diamino-2-propanol-N,N-diacetic acid.

EXAMPLE 1

(a) 244.0 g (2.0 moles) of salicylaldehyde was dissolved in 400 ml MeOH. 74.1 g (1.0 mole) of 1,3-propane-diamine in 100 ml of methanol was fed into the aldehyde over 1 hour from 20° C. to reflux. After being stirred for 2½ hours, the reaction mixture was cooled to 10° C., and the bright yellow crystals of N,N'-disalicylidine-1,3-propane-diamine (a Schiff's base) were filtered off. After drying in air, 277 g (98.2% yield) were obtained.

(b) 70.5 g (0.25 mole) of the above Schiff's base was reduced by adding it protionwise to 10.1 g (0.26 mole) NaBH₄ suspended in 250 ml of isopropanol over 30 minutes form 22°-57° C. The slurry was held at 50°-58° C. for 1½ hours. 150 ml of water was dripped in slowly with cooling, and the resultant thick mass was added to 2 l of water to precipitate the white amine. After stirring for a few minutes (ca. 10–15 minutes), the amine was filtered off, washed with water, and dried in air 55.8 g (78% yield) of N,N'-di(o-hydroxybenzyl)-1,3-propanediamine was obtained. (Other replications of step (a) and this step (step b) were run to prepare about 5 moles of N,N'-di(o-hydroxybenzyl)-1,3-propanediamine).

(c) 1662.0 g (4.56 moles) of N,N'-di-(o-hydroxybenzyl)-1,3-propanediamine was slurried in 6 l methanol at 50° C. 1,192 g (11.4 moles) of 54.5% glycolonitrile was added to the amine. Within 10 minutes the amine was dissolved. The solution was held at 40°–45° C. for 1¼ hours. After cooling for 45 minutes to 36° C., the nitrile precipitated. The product was filtered off an hour later at 26° C. and dried in air. 1,662.0 g (80% yield) of N,N'di(o-hydroxybenzyl)-1,3-propanediamine-N,N'-diacetonitrile was obtained.

(d) All of the above nitrile (4.56 moles) was dissolved in 3 l (about 36 moles) concentrated HCl acid. The solution was allowed to stand 5 days at room temperature. Some NH$_4$Cl and product hydrocholorides precipitated during this time. Then the reaction mixture was heated to 84° C. over 2 hours. The mixture was cooled to room temperature over 2 hours, its volume was doubled with water, and its pH was adjusted to 4.0 with 50% NaOH solution. Cooling was used to keep the mixture below 50° C. During the neutralization, the product hydrochlorides precipitated and were sampled. After complete neutralization with NaOH solution the slurry was stirred overnight. The product acid was filtered off, reslurried in 6 l of water, filtered off, and dried in air. 636 g (34.6% yield) N,N'-di(o-hydroxybenzyl)-1,3-propanedaimine-N,N'-diacetic acid (HBPD) was obtained. The HBPD was identified by elemental analysis, infrared spectroscopy, acid-base titration, and Cu$^{2+}$ titration.

EXAMPLE 2

13.2 g (0.069 mole) of 1,3-propanediamine-N,N'-diacetic acid (PDDA) was mixed with 36 g (0.38 mole) of phenol, 50 g of glacial acetic acid, and 50 ml of water. To this mixture 13.4 g (0.165 mole) of 37% formaldehyde dissolved in 125 ml of water was added with stirring. The pH was 2.6. The reaction mixture was left stirring unheated overnight. After two days standing at room temperature the mixture precipitated solid product. Two weeks later the reaction mixture was filtered to yield 13.0 g product, or 47% based on PDDA. After washing with acetic acid and acetone, the product produced a brillantly redcolored iron chelate in highly alkaline solutions. A gas chromotogram showed that the product was (HBPD)—the same product obtained in Example 1, supra.

EXAMPLE 3

62.6 g (0.1 mole) of 39.3% disodium hexahydropyrimidine-1,3-diacetate (HYPDANa$_2$) solution was acidified to pH 3 with concentrated hydrochloric acid to give a solution of 19 g (0.1 mole) of PDDA, 3 g (0.1 mole) of formaldehyde, and sodium chloride. An additional 6.9 g (0.1 mole) of 44% formaldehyde was added to said solution. The whole mixture was diluted to 100 ml with water and added to 37.6 g (0.4 mole) of phenol in 30 ml of methanol. The mixture was reacted and the product was isolated in the same manner as in Example 2. 16.0 g of 91.8% HBDP was obtained. Thus the equivalence of neutralized HYPDANa$_2$ solutions and PDDA/formaldehyde solutions in the preparation of HBPD was shown.

EXAMPLE 4

The general procedure of Example 3 was repeated except that an additional 13.8 g (0.3 mole) of 44% formaldehyde was added instead of 6.9 g. The yield was 20.8 g.

EXAMPLE 5

The general procedure of Example 4 was repeated. However, in this instance the methanol was omitted. The product precipitated as a sticky mass of soft lumps. The product mass was mixed with MeOH to get product solids, which were filtered off and washed with water and methanol. 29.5 g of 92% HBPD was obtained after drying at 50° C. or a 67.5% yield based on HYPDANa$_2$.

EXAMPLE 6

62.6 g (0.1 mole) of 39.3% HYPDANa$_2$ solution was acidified to pH 3.1–3.2 with about 18 ml of concentrated hydrochloric acid and 13.8 g (0.2 mole) of 44% formaldehyde was added. The resultant solution was mixed with 75.2 g (0.8 mole) of phenol and heated 16 hours at 70° C. The product was isolated as in Example 5. 36.8 g of 92.8% HBPD was obtained, or a 84.5% yield.

EXAMPLE 7

A reaction mixture was prepared by admixing 62.6 g of an aqueous system consisting essentially of water and HYPDANa$_2$ and analyzing 39.3% HYPDANa$_2$ (0.1 mole of HYPDANa$_2$), 13.8 g of an aqueous formaldehyde solution analyzing 44% HCHO (0.2 mole HCHO) and 41.8 g of an aqueous system consisting essentially of phenol and water and analyzing 90% phenol. (0.4 mole phenol). The pH of the reaction mixture was about 3. The reaction mixture was maintained at 70° C. for 16 hours and then cooled to about 25° C. The pH of the cooled reaction mixture was raised to 8 and the resultant solution was extracted with three 100 ml portions of ethyl ether. The aqueous layer was analyzed for HBPD by spectrophotometry (at 490 nm) of the solution after converting the HBPD product to its iron (III) chelate. The yield in solution was 84.3% based on HYPDANa$_2$ charged. In a similar run with a reaction time of eight hours the yield was 77.7%.

EXAMPLE 8

75.8 g (0.1 mole) of 34.6% disodium 5-hydroxyhexahydropyrimidine-1,3-diacetate was neutralized with hydrochloric acid to about pH 3 to give a solution of 20.6 g (0.1 mole) of 1,3-diamino-2-propanol-N,N'diacetic acid, 3 g (0.1 mole) of formaldehyde, and sodium chloride. 13.8 g (0.2 mole) of 44% formaldehyde was added to the solution. The resultant mixture was reacted with 37.6 g (0.4 mole) of phenol in 35 ml of MeOH at 60° C. for 16 hours. A thick white product slurry was obtained. The product was filtered off, slurried in MeOH, filtered, washed, and dried at 50° C. 13.2 g (32.5% yield) of N,N'-di(o-hydroxybenzyl)-1,3-diamino-2-propanol-N,N'-diacetic acid (HBPD-OL) was obtained.

EXAMPLE 9

43.2 g (0.4 mole) of m-cresol, 20.7 g (0.3 mole) of 44% CH$_2$O, and 62.6 g (0.1 mole) of HYPDANa$_2$ (neutralized to pH 3) in 150 ml of a 33% aqueous methanol solution was allowed to stand at room temperature for 15 days. The product that precipitated contained 8% m-cresol after washing. Isolation of the product as yielded 32.0 g, or 74% yield, of white N,N'-di(2-hydroxy-4-methyl-benzyl)-1,3-propanediamine-N,N'-diacetic acid.

EXAMPLE 10

55.6 g (0.4 mole) of p-nitrophenol was substituted for m-cresol in the general procedure of Example 9. 15 g of beige crystals were isolated. The product was identified as N,N'-di(2-hydroxy-5-nitrobenzyl)-1,3-propanediamine-N,N'-diacetic acid.

EXAMPLE 11

43.2 g (0.4 mole) of o-cresol was substituted for m-cresol in the general procedure of Example 9. 20 g of N,N'-di(2-hydroxy-3-methylbenzyl)-1,3-propanediamine-N,N'-diacetic acid was isolated.

EXAMPLE 12

17.7 g (0.1 mole) of ethylenediamine-N,N'-diacetic acid, 20.7 g (0.3 mole) of 44% CH$_2$O, and 37.6 g (0.4 mole) phenol in 90 ml water/30 ml methanol solution was stirred 20 days at room temperature (pH about 4.5). 4-(o-hydroxybenzyl)-2-piperazone-1-acetic acid was isolated as the major product by comparison to an authentic sample. This compound did not chelate iron. The remainder of the reaction mixture was mostly by-products, some unreacted material, and trace amounts of the desired N,N'-di-(o-hydroxybenzyl)ethylenediamine-N,N'-diacetic acid by gas chromatography.

EXAMPLE 13

28.0 g (0.1 mole) of N,N'-ethylenediaminedipropionic acid dihydrochloride was mixed with 50 ml of water and the pH was adjusted to 4.07 with 50% NaOH. 20.7 g (0.3 mole) of 44% formaldehyde and 75.2 g (0.8 mole) phenol were added. The mixture was heated with stirring at 70° C. for 16 hours. An oil layer separated. The addition of methanol gave a solution indicative of a polymeric and highly substituted mixture of products.

EXAMPLE 14

37.6 g (0.4 mole) of phenol, 13.8 g (0.3 mole) of 44% CH$_2$O, and 8.9 g (0.1 mole) of α-DL-alanine were dissolved in 100 ml of water and 30 ml of methanol, pH 5.5. After standing at room temperature for 20 days, the precipitated crystals of product were filtered from the reaction solution. The product was methanol soluble, indicating a non-specific mix of products. A clean sample was titrated with copper and was found to have an equivalent weight of 249.5 g versus 195.2 g for the monosubstituted product and 301.3 g for the di-substituted product, further indicating a mixture. The yield isolated was 3.5 g, or about 15%, depending on what the amount of substitution was.

PROCEDURE 1

The procedure of Example 9 can be used to prepare other ring-substituted HBPD chelating agents by replacing m-cresol with an equivalent amount of a phenol such as p-N,N-dimethylaminophenol, sodium p-phenolsulfonate, p-hydroxybenzoic acid, p-cyanophenol, 2,4-dimethylphenol or the like. Analogous ring-substituted N,N'-di(o-hydroxybenzyl)-1,3-diamino-2-propanol-N,N'-diacetic acids can be prepared by using 1,3-diamino-2-propanol-N,N'-diacetic acid instead of PDDA.

PROCEDURE 2

A product amine having the formula

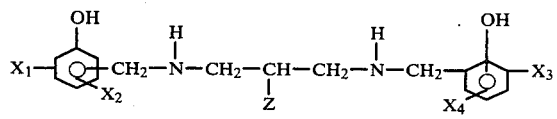

in which Z is —H or —OH and each of $X_1$, $X_2$, $X_3$, and $X_4$ is of hydrogen, —OH, an alkyl group having 1–4 carbon atoms, —CN, —SO$_3$M, or —COOM in which M is a hydrogen ion, and alkali metal ion, ½ an alkaline earth metal ion, or an ammonium ion having the formula

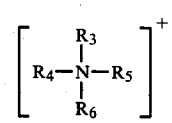

in which each of $R_3$, $R_4$, $R_5$, and $R_6$ is hydrogen, an alkyl group having 1–4 carbon atoms, a hydroxyalkyl group having 1–4 carbon atoms, or an alkyl group having 1–4 carbon atoms can be prepared by using the general method of the first two paragraphs of Example 1 wherein the method is modified by replacing the salicylaldehyde with aldehyde(s) having the formula(s)

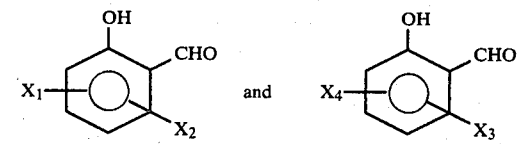

If it is desired to have $X_1$ and $X_2$ identical with $X_3$ and $X_4$, respectively, only one aldehyde is used, otherwise two aldehydes are used.

In such method: (a) the use of 1,3-propanediamine (as in Example 1) will produce a product amine in which Z is —H; and (b) the use of 1,3-diamino-2-propanol rather than 1,3-propanediamine will produce a product amine in which Z is —OH.

Where using two aldehydes, a mixture of three product amines will be obtained, to wit:

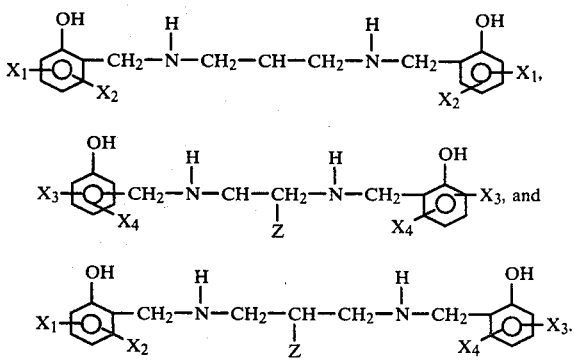

It will be observed that in the foregoing Examples 1–11, an acid pH is used and a high, isolable yield of the desired product is obtained. In contrast, Examples 12-14 illustrate that even in an acidic medium not all diamino acids give high, isoluble yields. Thus, it is the unique combination of both the acidic medium and the particular trimethylene diamino acids of the present invention which give the unexpected results of obtaining the desired compounds in high, isoluble yields and a novel process for preparing such compounds.

TABLE I

| Example | pH | % Yield |
|---------|------|---------|
| 1 | 4.0 | 34.6 |
| 2 | 2.6 | 47.0 |
| 3 | 3.0 | 36.5 |
| 4 | 3.0 | 47.4 |
| 5 | 3.0 | 67.5 |
| 6 | 3.0 | 84.5 |
| 7 | 3.0 | 84.3 |
| 8 | 3.0 | 32.5 |
| 9 | 3.0 | 74.0 |
| 10 | 3.0 | 38.6 |
| 11 | 3.0 | 46.2 |
| 12 | 4.5 | — |
| 13 | 4.07 | — |
| 14 | 5.5 | 15 |

For purposes of further illustrating the advantages of using an acidic pH with the particular diamino acids of the present invention, the following compound ("Compound A") was prepared according to Example 9 of U.S. Pat. No. 4,069,249

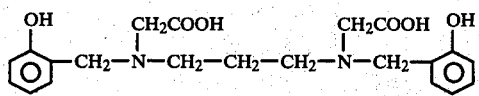

and its stability tested at various pH's according to the Hampshire Stability Test as follows:

TEST A 200 mg of Compound A was mixed with about 150 ml of water and dissolved therein to form a first resulting solution by adding aqueous 8% sodium hydroxide solution dropwise while stirring.

A second resulting solution was formed by adjusting the pH of the first resulting solution to 8 with an aqueous 85% solution of phosphoric acid, and a test solution was prepared by diluting the second resulting solution to 200 ml with water.

A 10 ml sample of the test solution was taken for analysis while the remainder of said solution was tested for stability.

It was calculated that the concentration of Compound A in the test solution should be 1 mg per ml and spectrophotometric analysis confirmed this.

The remainder of the test solution (from which the 10 ml aliquot has been taken) was placed in a stirred 250 ml, 3-neck, round-bottom flask provided with a condenser and heated on a water bath at 80° C. Samples (10 ml aliquots into tared 50 ml volumetric flasks) were taken through the condenser at hourly intervals for each of the first 4 hours of heating and after 21 hours heating. The Compound A content of each sample was determined spectrophotometrically. The results of these determinations are reported in Table II.

TEST B

The method used in Test A was repeated using Compound A, in this instance:

(a) The respective test solution contained 600 mg of the compound (Compound A) rather than 200 mg as in Test A.
(b) The pH was adjusted to 6.
(c) The heating bath temperature was 85° C.
(d) Samples were taken hourly for 5 hours but not after 21 hours.

The results obtained are presented in said Table II.

TEST C

The method used in Test B was repeated using Compound A in this instance:

(a) The respective test solution contained 450 mg of the compound (Compound A) in 150 ml of solution (total volume of solution).
(b) The pH of the solution prepared from Compound A had a pH of 4 without further adjustment.
(c) The heating bath temperature was 90° C.
(d) Samples were taken hourly during the first 5 hours heating and at the end of 21 hours heating.

The results obtained are presented in said Table II.

TEST D

The method of Test C was repeated; however, in this instance:

(a) The pH of the test solution was adjusted to 2 with dilute (6 normal) hydrochloric acid.
(b) Samples were taken hourly during heating for 5 hours but not after 21 hours.

The results obtained are presented in said Table II and clearly indicate the greater stability of the desired end product at acidic pH values.

TABLE II

| THE HAMPSHIRE STABILITY TEST Stability of Compound A as Percent Remaining After Heating at the Recited pH and Temperature | | | | |
|---|---|---|---|---|
| Heating Time (hrs) | pH=8 at 80° C. | pH=6 at 85° C. | pH-4 at 90° C. | pH=2 at 90° C. |
| 1 | 67.5 | 73.8 | 97.8 | 100.0 |
| 2 | 50.8 | 57.5 | 94.9 | 99.0 |
| 3 | 42.6 | 44.9 | 91.6 | 97.8 |
| 4 | 36.4 | 38.0 | 88.8 | 97.1 |
| 5 | — | 32.2 | 85.8 | 95.9 |
| 21 | 8.9 | — | 42.0 | — |

We claim:

1. A process for preparing an ortho-substituted phenolic amino acid compound having the formula:

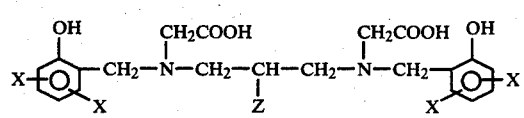

wherein:
(a) Z is H or OH; and
(b) each X is selected from a group consisting of hydrogen; an alkyl group having 1-4 carbon atoms; —COOH; and —SO₃M, wherein M is selected from a group consisting of an alkali metal ion, ½ of an alkaline earth metal ion, and an ammonium ion having the formula

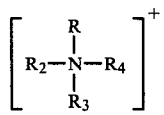

in which each of $R_1$, $R_2$, $R_3$ and $R_4$ is selected from a group consisting of hydrogen, an alkyl group having 1–4 carbon atoms, and a hydroxyalkyl group having 1–4 carbon atoms; said process comprising:

(i) forming a resulting mixture by admixing:
   (a) an inert reaction medium selected from a group consisting of water, methyl alcohol, ethyl alcohol, isopropyl alcohol, n-propyl alcohol, an admixture of water and the alcohol, acetic acid, and an admixture of water and acetic acid;
   (b) a phenol or mixture of phenols, each having the formula

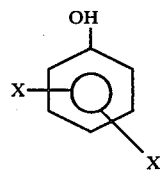

(c) an acid having the formula

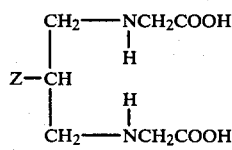

or a source of this acid, said source having the formula

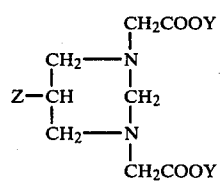

in which Y is an alkali metal ion, ½ of an alkaline earth metal ion, or the ammonium ion having the formula

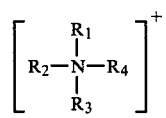

(d) a formaldehyde source selected from a group consisting of an aqueous formaldehyde solution, trioxane, and paraformaldehyde; and
(ii) maintaining the resulting mixture at a temperature and for a time effective for forming the compound, and at a pH of about 2 to about 6, the inert reaction medium being provided in an amount effective for dissolving the phenol.

2. The process of claim 1 in which the phenol is

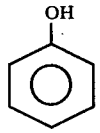

3. The process of claim 1 in which the phenol is

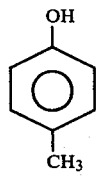

4. The process of claim 1 in which the phenol is

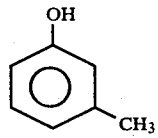

5. The process of claim 1 in which the phenol is

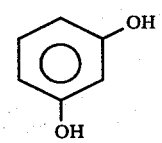

6. The process of claim 1 in which the phenol is

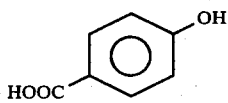

7. The process of claim 1 in which the acid is provided as a solution of the acid source, said source having the formula

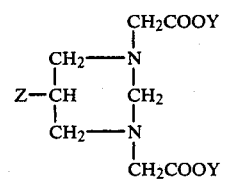

* * * * *